United States Patent [19]

Hill

[11] Patent Number: 5,449,522

[45] Date of Patent: Sep. 12, 1995

[54] PHARMACEUTICAL COMPOSITION FOR IMMUNOENHANCEMENT THERAPY

[76] Inventor: Albert F. Hill, 1755 Monaco Pkwy., Denver, Colo. 80220

[21] Appl. No.: 111,288

[22] Filed: Aug. 24, 1993

[51] Int. Cl.[6] ...................... A61K 33/14; A61K 35/55
[52] U.S. Cl. ................................... 424/722; 424/679; 424/717; 424/568; 514/4; 514/23; 514/397
[58] Field of Search ...................... 514/885, 4, 23, 397, 514/; 424/679, 717, 722, 400, 568

[56] References Cited

U.S. PATENT DOCUMENTS 4,196,196  4/1980  Tiholiz .
4,971,951  11/1990  Garcia y Bellon et al. ............ 514/4
5,077,284  12/1991  Loria et al. .......................... 514/885

OTHER PUBLICATIONS

Old, L. J. (1988), "Tumor Necrosis Factor," Scientific American 258:59–75.
Patillo, R. (1974) "Trophoblast Cancers," in Hormones and Cancer, (K. W. McKerns, ed.), Academic Press, New York, p. 363–387.
Prehn, R. T. (1976), "Do Tumors Grow because of the Immune Response of the Host°" Transplantation Reviews 28:34–42.
Ellenhorn, J. D. et al. (1988), "In vivo Administration of Anti-CD3 Prevents Malignant Progressor Tumor Growth," Science 242:569–571.
Golde, D. W. et al. (1988), "Hormones that Stimulate the Growth of Blood Cells," Scientific American 259:62–70.
Bevilacqua M. P. et al. (1989), "Endothelial Leukocyte Adhesion Molecule 1: an Inducible Receptor for Neutrophils Related to Complement Regulatory Proteins and Lectins," Science 243:1160.
Oppenheim, J. J. et al. (1987), in Basic and Clinical Immunology, Sixth ed., (D. P. Stites, et al., eds.), Appleton and Lange, Los Altos, CA, p. 94.
Rosenberg, S. A. et al. (1986), "A New Approach to the Adoptive Immunotherapy of Cancer with Tumor-infiltrating Lymphocytes," Science 233:1318–1321.
Geiger, J. D. et al. (1993), "Generation of T-Cells Reactive to the Poorly Immunogenic B16–BL6 Melanoma with Efficacy in the Treatment of Spontaneous Metastases," J. Immunother. 13:153–165.
Chang, A. E. et al. (1993), "Clinical Observations on Adoptive Immunotherapy with Vaccine-primed T-Lymphocytes Secondarily Sensitized to Tumor In Vitro," Cancer Res. 53:1043–1050.
Handwerger, B. S. and Douglas, S. D., (1980) "The Cell Biology of Blastogenesis," in The Cell Biology of Inflammation, (G. Weismann, ed.), Elsevier, New York/N. Holland Biomedical Press, Amsterdam, p. 652–657.
Lawrence, T. S. and Davis, M. A. (1990), "The Influence of $Na^+$, $K^+$–pump Blockade on Doxorubicin-mediated Cytotoxicity and DNA Strand Breakage in Human Tumor Cells," Cancer Chemother. and Pharmacol. 26:163–67.
Owens, T. and Kaplan, J. G. (1981), "Monovalent Cation Fluxes in Activated Mouse T- and B-Lymphocytes," in Mechanisms of Lymphocyte Activation (Resch, K. and Kirchner, H. eds.) pp. 238–241.
Grinstein, S. and Dixon, S. J. (1989), "Ion Transport, Membrane Potential, and Cytoplasmic pH in Lymphocytes: Changes during Activation," Physiol. Rev. 69:417–481.
Cahalan, M. D. et al. (1991), "Potassium Channels in Development, Activation, and Disease in T-Lymphocytes," in Developmental Biology of Membrane Transport Systems (Benos, D. J., ed.), pp. 357–394.

(List continued on next page.)

Primary Examiner—Frederick Krass
Assistant Examiner—Amy Hulina
Attorney, Agent, or Firm—Greenlee and Winner

[57] ABSTRACT

This invention provides an immunoenhancement or immunepotentiation therapy comprising administration of potassium, insulin, glucose and, optionally, thyroid, a cholinergic agent and bicarbonate. Therapeutic compositions comprising the above components in appropriate dosages are also provided.

7 Claims, 1 Drawing Sheet

LIFE SURVIVAL GRAPH FOR CANINES

● = % Survival Actual
■ = % Survival Expected

OTHER PUBLICATIONS

Gerson, M., A Cancer Therapy: Results of Fifty Cases, (New York: Dura Books, Inc., 1958), pp. 237–248.

Edgington, S. M. (1993), "Looking Death in the Eye: Apoptosis and Cancer Research—Is Cancer really Caused by Cells Refusing to Commit Suicide on Cue?," Bio/Tech. 11:787–792.

Hardin, J. A., et al., (1992), "A Simple Fluorescence Method for Surface Antigen Phenotyping of Lymphocytes Undergoing DNA Fragmentation," J. immuno. Meth. 154:99–107.

Ojcius, D. M., et al. (1991), "Ionophore–Induced Apoptosis: Role of DNA Fragmentation and Calcium Fluxes," Exp. Cell. Res. 197:43–49.

McGrady, P. (1964), The Savage Cell, Basic Books, Inc., New York, p. 138–140.

Kassirer, Jerome P., (1989), "Repairing Body Fluids: Principles and Practice," p. 46–72.

Koffler, Michael, et al. (1991), "Immunobiological Consequence of Regulation of Insulin Receptor on Alloactivated Lymphocytes in Normal and Obese Subjects," Diabetes 40:364–370.

Coffey, Ronald G. and Hadden, John W. (1984), "Cyclic Nucleotides in Neurohumoral and Hormonal Regulation of Cells of the Immune System," in Stress, Immunity and Aging (Cooper, E. L., ed.) pp. 231 ff.

Strom, Terry B., et al. (1975), "Insulin–Induced Augmentation of Lymphocyte–Mediated Cytotoxicity," Science 187:1206–1208.

Ercolani, L., et al. (1985), "Insulin–Induced Desensitization at the Receptor and Postreceptor Level in Mitogen–Activated Human T–lymphocytes," Diabetes: 34:931–937.

Morrison, S. D. (1982), "Feeding Responcse of Tumor–bearing Rats to Insulin Withdrawl and the Contribution of Autonomous Tumor Drain to Cachectic Depletion," Cancer Res. 42:3642–3647.

Moley, J. F., et al. (1985), "Insulin Reversal of Cancer Cachexia in Rats," Cancer Res. 45:4925–4931.

Moley, J. F., et al. (1983), "Effects of Exogenous Insulin Administration on Food Intake, Body Weight Change, and Tumor Doubling Time," Surgical Forum 35:91–93.

Schein, Philip S., et al. (1979) "Cachexia of Malignancy," Cancer 43:2070–2076.

Strom, T. B., et al. (1977), "The Role of Cyclic Nucleotides in Lymphocyte Activation and Function," in Progress in Clinical Immunology (Schwartz, R. S., ed.) at 115–153.

Ignarro, L. J. and Cech, S. Y. (1976), "Bidirectional Regulation of Lysosomal Enzyme Secretion and Phagocytosis in Human Neutrophils by Guanosine 3', 5'–Monophosphate and Adenosine 3', 5'–Monophosphate (39232)," Proc. Nat. Acad. Sci. 151:448–452.

Unanue, E. R. and Schreiner, G. F. (1975), "The Modulation of Immunoglobulin in B Lympocytes and its Relevance to Immune Stimulation," Immune Recognition (Rosenthal, A. S., ed.) at 261–280.

Kasner, S. E. and Ganz, M. B. (1992), "Regulation of intracellular potassium in mesangeal cells: a fluorescence analysis usin the dye, PBFI," Amer. J. Physiol. 3:462–467.

Provinciali, M., et al. (1992), "Optimization of Cytoxic Assay by Target Cell Retention of the Fluorescent Dye Carboxyfluorescein Diacetate (CFDA) and Comparison with Conventional $^{51}$Cr Release Assay," J. Immunol. Meth. 155:19–24.

Vollenweider, I. and Groseurth, P. J. (1992), "Comparison of the Four DNA Staining Fluorescence Dyes for Measuring Cell Proliferation of Lymphokine–activated killer LAK) Cells," J. Immunol. Meth. 149:133–135.

Loeffler, D. A., et al. (1992), "Analysis of Distribution of Tumor– and Preneoplasia–Infiltrating Lymphocytes Using Simultaneous Hoechst 33342 Labeling and Immunophenotyping," Cytom. 13:169–174.

Rivoltini, L., et al (1992), "Phenotypic and Functional Analysis of Lymphocytes Infiltrating Paediatric Tumours, with a Characterization of the Tumour Phenotype," Can. Immunol. Immunother. 34:241–251.

Harold, F. M. (1986) The Vital Force: A Study of Bioenergetics, W. H. Freeman and Co., New York, pp. 325–326.

Segel, G. B. and Lichtman, M. A. (1976), "Potassium Transport in Human Blood Lymphocytes Treated with Phytohemagglutinin," J, Clin. Investigation 58:1358–1359; 1365–1366.

Quastel, M. R. and Kaplan, J. G. (1970) "Early Stimulation of Potassium Uptake in Lymphocytes Treated with PHA," Expl. Cell. Res. 63:230–233.

Ignarro, L. J. (1975), "Regulation of Lysosomal Enzyme Release by Prostaglandins, Autonomic Neurohor-

OTHER PUBLICATIONS

-mones and Cylic Nucleotides," in Lysosomes in Biology and Pathology (Dingle, J. T. and Dean, R. T., eds.) pp. 481–523.

Hadden, J. W. (1987), "Neuroendocrine Modulation of the Thymus–Dependent Immune System," Annals of the N.Y. Acad. of Sciences 496:39–48.

Tiedt, T. N. et al. (1979) "Voltage- and Time-Dependent Actions of Piperocaine on the Ion Channel of the Acetylcholine Receptor," Molec. Pharmacology 16:909–921.

Rosenberg, S. A. (1990), "Adoptive Immunotherapy for Cancer," Scientific American 262:62–69.

PHARMACEUTICAL COMPOSITION FOR IMMUNOENHANCEMENT THERAPY

FIELD OF THE INVENTION

This invention is in the field of immunoenhancement therapy and compositions useful therefor.

BACKGROUND OF THE INVENTION

Since Jenner successfully vaccinated a patient against smallpox more than 200 years ago, physicians have sought ways to enhance immunity to deal with other diseases. Immunization in several forms has led to the elimination of serious consequences or even deaths from a number of diseases such as poliomyelitis, diphtheria, pertussis, typhoid fever, mumps and rubella.

Enhancement of immunity is a desirable goal in the treatment of patients diagnosed with cancer, immune deficiency syndrome, certain topical and systemic infections, leprosy, tuberculosis, shingles, warts, herpes, malaria, gingivitis, atherosclerosis, and others.

Almost a hundred years ago William Coley tried to enlist the aid of the immune system against cancer. He had some success in treating cancer patients by infecting them with live bacteria. However, the infections caused such serious problems for the patients that he turned to the development of vaccines based on killed bacteria (Old, L. J. (1988), "Tumor Necrosis Factor," Scientific American 258:59–60). These preparations were called Coley's toxins. He achieved only limited success. Soon radiation and chemotherapy supplanted his toxins as the therapy of choice.

However, investigators continued to be fascinated with the possibility of enhancing immunity to destroy tumors. Lewis Thomas and Macfarlane Burnet gave impetus to the movement when they suggested in their Theory of Immune Surveillance that the body routinely must deal with mutations and therefore carries on a constant surveillance for such rogue cells. The recognition that human tumors are immunogenic to the host and therefore do provoke an immune response, albeit inadequate, has caused investigators to hope that immunotherapy for cancer is possible. (Patillo, R. (1974) "Trophoblast Cancers," in Hormones and Cancer, (K. W. McKerns, ed.), Academic Press, New York, p. 384; Prehn, R. T. (1976), "Do Tumors Grow because of the Immune Response of the Host?" Transplantation Reviews 28:34–42; Ellenhorn, J. D. et al. (1988), "In vivo Administration of Anti-CD3 Prevents Malignant Progressor Tumor Growth," Science 242:569–571.

Rare but indisputable spontaneous regressions of tumors, often after an infection, provided still further encouragement. The exquisite specificity of the immune system, its ability to provide resistance to infections and to destroy transplants, gave promise that enhanced immunity would be the ideal treatment for cancer. However, there have been many attempts but with only limited results.

The first breakthrough in understanding immune regulation was provided by the Clonal Selection Theory developed by David Talmage, Niels Jerne and Macfarlane Burnet, proposing that when antigen and lymphocyte receptor match, the lymphocyte is "selected" for activation and proliferation. However, despite the enormous contribution of the concept of clonal selection to the understanding of immune regulation, little progress has been made in finding a way to enhance immunity. The clinician could reduce immune reactions with such agents as cyclosporine or the glucocorticoids, but he could not increase it.

The second important clue came with the discovery of a group of lymphokines and cytokines. Antigen-non-specific modulatory proteins released primarily, but not exclusively, by immune cells were shown to regulate the magnitude of the immune response. While only antigen binding could select the cell that would expand into a clone, that cell could proliferate only if it also received stimulation from one or more of these proteins. Some of these substances, such as the interferons or interleukin-1 or -2, directly stimulate the immune cells. Others stimulate the bone marrow to produce more leukocytes. (Golde, D. W. et al. (1988), "Hormones that Stimulate the Growth of Blood Cells," Scientific American 259:62–71).

Some act as chemoattractants to macrophages and polymorphonuclear leukocytes, induce receptors on endothelial cells so that circulating leukocytes stick to them (Bevilacquam M. J. et al. (1989), "Endothelial Leukocyte Adhesion Molecule 1: an Inducible Receptor for Neutrophils Related to Complement Regulatory Proteins and Lectins," Science 243:1160) and cause endothelial cells to part so leukocytes can leave the vascular compartment and enter the wound. Some are potent angiogenic factors, stimulating replacement of vessels in injured tissue. Some immobilize phagocytes to prevent their wandering away from the wound. Others activate macrophages to phagocytose debris and pathogens and to produce more factors (e.g., cachectin and interleukin-1). Fibroblasts are stimulated to lay down fibrin barricades to restrict pathogens to the local area. One cytokine, cachectin (Tumor Necrosis Factor-alpha), appears to be the substance responsible for the effects Coley witnessed. (Old, L. J. (1988), "Tumor Necrosis Factor," Scientific American 258:59–60.)

There have been massive efforts to enlist the assistance of these substances to enhance immunity and to provoke an attack on tumors. Some success has been achieved. Interferon-alpha, produced primarily by leukocytes, has been effective in treating low-grade non-Hodgkin's lymphoma, cutaneous T cell lymphoma, chronic myelogenous leukemia, Kaposi's sarcoma and especially hairy cell leukemia. For reasons not fully understood, it seems to have little effect on some patients and no effect on tumors other than those listed above. (Oppenheim, J. J. et al. (1987), in *Basic and Clinical Immunology*, Sixth ed., (D. P. Stites, et al., eds.), Appleton and Lange, Los Altos, Calif., p. 94.

Efforts to use cachectin to provoke an inflammation that will be destructive of tumors have produced frustratingly inconsistent results and dangerous toxicity. (Old, L. J. (May 1988), "Tumor Necrosis Factor," Scientific American 258:59–60.)

Interleukin-2, produced by helper T cells, has been intensively studied for its effect on tumors. In the most successful of these studies, lymphocytes that have infiltrated a tumor are activated in vitro by IL-2. When the cells have proliferated to significant amounts they, with additional IL-2, are injected into the patient. (Rosenberg, S. A. et al. (1986), "A New Approach to the Adoptive Immunotherapy of Cancer with Tumor-infiltrating Lymphocytes," Science 233:1318–1321; Rosenberg, S. A., (1990), "Adoptive Immunotherapy for Cancer," Scientific American 262:62–69; Geiger, J. D. et al. (1993), "Generation of T-Cells Reactive to the Poorly Immunogenic B16-BL6 Melanoma with Efficacy in the Treatment of Spontaneous Metastases," J. Immunother. 13:153–165; Chang, A. E. et al. (1993), "Clinical Observations on Adoptive Immunotherapy with Vaccine-primed T-Lymphocytes Secondarily Sensitized to Tumor In Vitro," Cancer Res. 53:1043–1050.) The experiments have been partially successful in treating colon and kidney cancer and malignant melanoma. About 20% of the patients show at least some response. A few have been symptom-free for months. Unfortunately, IL-2 has been shown to be toxic in the amounts most helpful in dealing with the tumor. (Oppenheim, J. J. et al. (1987), in Basic and Clinical Immunology, Sixth ed., (D. P. Stites, et al., eds.), Appleton and Lange, Los Altos, Calif., p. 94; Petska, S. (ed.), (January 1992), "Current Approaches and Obstacles to Immunotherapy, Pharm Tech., pp 26–35) Toxic effects include malaise, fever, nausea or vomiting, diarrhea and anemia. A nontoxic method for stimulating selected lymphocytes in vivo or in vitro is therefore needed.

When a lymphocyte is selected by antigen, the first detectable effect is an efflux of potassium and a compensating influx of sodium, down the electrochemical gradient. Before the lymphocyte can respond to stimulation by cytokines, it must restore intracellular levels of potassium to normal with the sodium/potassium pump ($Na^+K^+$ ATPase), an energy-dependent action. A number of investigators have shown that blockage of the $Na^+K^+$ ATPase will prevent the cell from activating or proliferating. (See, e.g., Ward, P. A., (1985) "Inflammation," in Immunology III, (J. A. Bellanti, ed.), W. B. Saunders, Co., Philadelphia, Pa., p. 212; Handwerger, B. S. and Douglas, S. D., (1980) "Cell Biology of Blastogenesis," in The Cell Biology of Inflammation (G. Weissmann, ed.), Elsevier, New York/N. Holland Biomedical Press, Amsterdam, p. 654.) Tumor cells have been reported to become resistant to chemotherapy and it has been suggested that stimulation of the sodium-potassium ion pump might reverse this drug resistance. Lawrence, T. S. and Davis, M. A. (1990), "The Influence of Na, K-pump Blockade on Doxorubicin-mediated Cytotoxicity and DNA Strand Breakage in Human Tumor Cells," Cancer Chemother. and Pharmacol. 26:163–167.

While others have noted that normal intracellular potassium stores are essential for lymphocyte activation (Owens, T. and Kaplan, J. G. (1981), "Monovalent Cation Fluxes in Activated Mouse T- and B-Lymphocytes," in Mechanisms of Lymphocyte Activation (Resch, K. and Kirchner, H. eds.) pp. 238–241; Grinstein, S. and Dixon, S. J. (1989), "Ion Transport, Membrane Potential, and Cytoplasmic pH in Lymphocytes: Changes during Activation," Physiol. Rev. 69:417–481; Calahan, M. D. et al. (1991), "Potassium Channels in Development, Activation, and Disease in T Lymphocytes," in Developmental Biology of Membrane Transport Systems (Benos, D. J., ed.), pp. 357–394), there has been no recent effort to activate immunity through potassium repletion. In the 1940's Dr. Max Gerson devised a nutritional treatment for cancer that included oral administration of various potassium salts. Although he claimed some success, the medical society of New York declared his method of no value. Gerson's therapy attained some fame when he treated the young son of John Gunther for a brain tumor. The boy died. Gerson's therapy is described in his book, A Cancer Therapy: Results of Fifty Cases, (New York: Dura Books, Inc., 1958), pp. 237–248. Although he is deceased, patients are still treated with revised versions of his therapy in Mexico.

The phenomenon of faulty apoptosis or cell suicide has also been implicated in cancer etiology. (Edgington, S. M. (1993), "Looking Death in the Eye: Apoptosis and Cancer Research—Is Cancer really Caused by Cells Refusing to Commit Suicide on Cue?" Bio/Tech 11:787–792; Hardin, J. A., et al (1992), "A Simple Fluorescence Method for Surface Antigen Phenotyping of Lymphocytes Undergoing DNA Fragmentation," J. Immuno. Meth. 154:99–107.) It has been suggested that potassium has a role in triggering apoptosis in cells (Ojcius, D. M., et al. (1991), "Ionophore-Induced Apoptosis: Role of DNA Fragmentation and Calcium Fluxes," Exp. Cell Res. 197:43–49).

Thyroid-suppressing drugs and thyroid removal have been shown to increase the virulence of all categories of cancers, carcinogen-induced, transplanted and spontaneous. Statistics relate cancer inversely to thyroid function, with the disease being most common among hypothyroid people and least frequent in hyperthyroids. In one study, breast cancer was nine times as common among extremely hypothyroid and sixteen times as common among thyroidectomized women as among hyperthyroid women. In the early 1950's, Dr. Alfred A. Loeser administered thyroid to breast cancer patients with good results. Others found virtually no response. (McGrady, P. (1964), The Savage Cell, Basic Books, Inc., New York, p. 139.)

It has been known for years that insulin lowers serum potassium concentration. (Kassirer, Jerome P., et al. (1989), in Repairing Body Fluids: Principles and Practice, p. 47). And, it is established that insulin, like many other hormones, neurotransmitters and autacoids, participates in the regulation of immune responses, particularly T-lymphocyte function (Koffler, Michael, et al. (1991), "Immunobiological Consequence of Regulation of Insulin Receptor on Alloactivated Lymphocytes in Normal and Obese Subjects," Diabetes 40:364–370; Coffey, Ronald G. and Hadden, John W. (1984), "Cyclic Nucleotides in Neurohumoral and Hormonal Regulation of Cells of the Immune System," in Stress, Immunity and Aging (Cooper, E. L., ed.) pp. 231 ff.).

When it was discovered that lymphocytes present insulin receptors late in their cycle, investigators studied the effect of the hormone on these leukocytes in vitro. Their studies showed that physiological concentrations of insulin enhance the ability of cytotoxic lymphocytes to injure target cells. Since insulin seemed to have much the same immune enhancing effect as cholinergic agents and to function in the same time- and dosage-dependent way, it was hypothesized they worked through the same receptor. However, studies with the muscarinic antagonist, atropine, established that the insulin-induced augmentation of lymphocyte-mediated cytotoxicity (LMC) was independent of the cholinergic receptor (Strom, Terry B., et al. (1975), "Insulin-Induced Augmentation of Lymphocyte-Mediated Cytotoxicity," Science 187:1206–1208). Furthermore, while cholinergic agents cause an increase in cyclic GMP, one investigator was unable to demonstrate any effect of insulin on cytosolic cyclic GMP or AMp, before or after acquisition of its insulin receptor (Ercolani, L., et al (1985), "Insulin-Induced Desensitization at the Receptor and Postreceptor Level in Mitogen-Activated Human T-lymphocytes," Diabetes 34:931–937).

It was discovered that lymphocytes could regulate the number of insulin receptors on their membranes. Stimulation by insulin declined as the receptors decreased. Furthermore, an inverse relationship was shown to exist between the concentration of plasma insulin and the ultimate display of receptors. Studies employing the euglycemic clamp technique showed that chronic hyperinsulinemia in vivo caused the number of receptors on cytotoxic T-lymphocytes to decline from 6752 to 1665 per cell, with a corresponding loss of killing effectiveness. Furthermore this loss of cytotoxicity continued in vitro for several hours, despite being placed in low insulin media (Koffler, Michael, et al. (1991), "Immunobiological Consequence of Regulation of Insulin Receptor on Alloactivated Lymphocytes in Normal and Obese Subjects," Diabetes 40:364–370).

A number of investigators studied the effects of insulin on cachexia in tumor-bearing animals. In general they found that it reversed the anorexia and produced a weight gain but did not prolong survival or have any effect on the tumor (Morrison, S. D. (1982), "Feeding Response of Tumor-bearing Rats to Insulin and Insulin Withdrawal and the Contribution of Autonomous Tumor Drain to Cachectic Depletion," Cancer Res. 42:3642–3647; Moley, J. F., et al (1985), "Insulin Reversal of Cancer Cachexia in Rats, Cancer Res. 45:4925–4931; Moley, J. F., et al. (1983), "Effects of Exogenous Insulin Administration on Food Intake, Body Weight Change, and Tumor Doubling Time," Surgical Forum 35:91-93). Schein, Philip S., et al (1979), "Cachexia of Malignancy," Cancer 43:2070–2076, reported that patients manifesting cachexia of malignancy showed a marked resistance to administered insulin while insulin receptors on monocytes were normal.

Almost thirty years ago, Dr. Oscar Neufeld found similarities between the cachexia of cancer and the wasting in diabetes, and he decided to give insulin to seven patients (three who had cancers of the lung, two of the esophagus, and one each of the liver and stomach). His aim was to stimulate their appetites. In all but one (the stomach-cancer patient), appetite returned; and all of them gained weight and felt better; some experienced a feeling of euphoria. The gradually-increased insulin doses were generally well tolerated. (McGrady, P. (1964), The Savage Cell, Basic Books, Inc., New York, p. 139.)

In 1958, some British, Canadian and American scientists found that insulin had no therapeutic effect on mouse and rat transplanted tumors, although a combination of insulin and glucagon in toxic doses slowed down many of these cancers. Glucagon alone also arrested these cancers. (McGrady, P. (1964), The Savage Cell, Basic Books, Inc., New York, p. 139–140.)

An increase in cyclic GMP is thought to act as an early signal controlling lymphocyte transformation and proliferation of resting lymphocytes. Acetylcholine and muscarinic cholinergic agents such as pilocarpine are known to raise intracellular levels of cyclic GMP in human lymphocytes. Cholinergic agents also enhance lymphocyte mediated cytotoxicity (LMC) in sensitized cells. Strom, T. B., et al (1977), "The Role of Cyclic Nucleotides in Lymphocyte Activation and Function," in Progress in Clinical Immunology (Schwartz, R. S., ed.) at 115-153. Acetylcholine and agonists stimulate the immunologic secretion of beta-glucuronidase and enhance phagocytosis in neutrophils. Ignarro, L. J. and Cech S. Y. (1976), "Bidirectional Regulation of Lysosomal Enzyme Secretion and Phagocytosis in Human Neutrophils by Guanosine 3',5'-Monophosphate and Adenosine 3',5'-Monophosphate (39232)," Proc. Nat. Acad. Sci. 151:448–452. It has also been shown that cholinergic effects are exerted on hematopoietic stem cells. (Unanue, E. R. and Schreiner, G. F. (1975), "The Modulation of Immunoglobulin in B Lymphocytes and its Relevance to Immune Stimulation," in Immune Regulation (Rosenthal, A. S., ed.) at 271.)

Nontoxic treatments for enhancing immune response have been sought, but to date an effective treatment has not been available.

SUMMARY OF THE INVENTION

Figure 1:
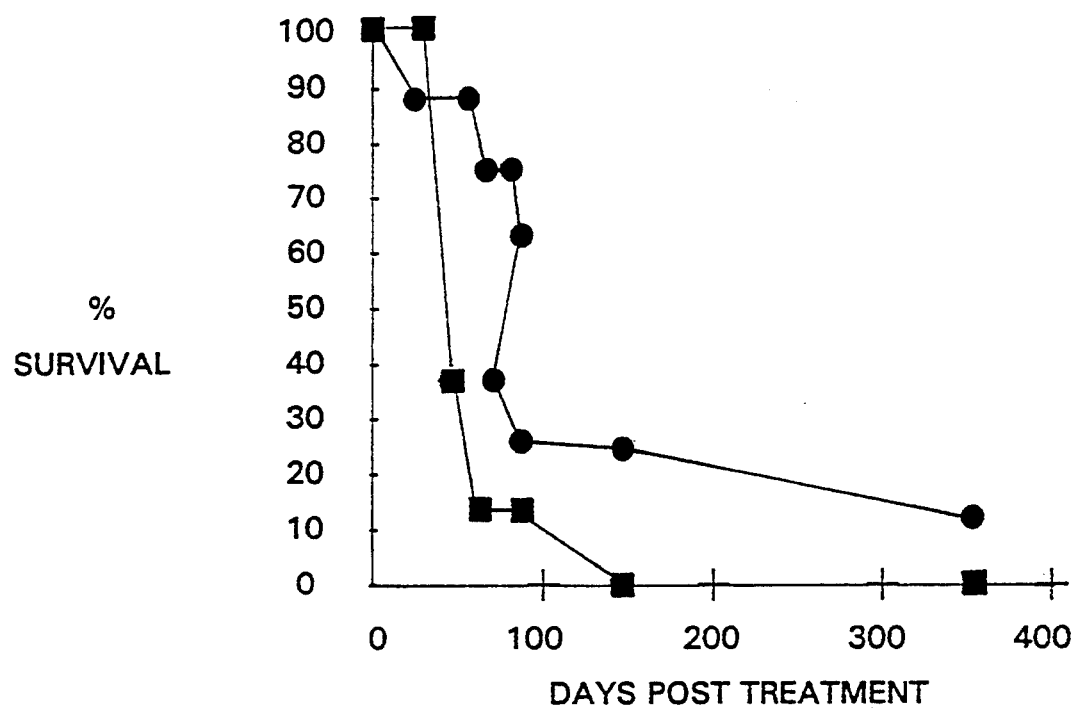
FIG. 1 is a graph comparing actual survival time with expected survival time for eight dogs with mixed tumor types undergoing the treatment regimen of this invention.

This invention provides compositions and methods of using such compositions, comprising a number of compounds, for intracellular repletion and accumulation of potassium in mammals including humans. Methods are provided for increasing the intracellular potassium content of lymphocytes of a mammal, preferably lymphocytes which have been previously selected by antigen, comprising administering to said mammal an effective amount of insulin or insulin-producing compounds, glucose and pharmaceutically acceptable equivalents thereof, and potassium. Thyroid hormones singly or in pharmaceutical combinations, bicarbonate and pharmaceutical salts thereof, and cholinergic agents such as acetylcholine, pilocarpine and carbachol also may be administered.

As used herein, the term "insulin" includes insulin-producing drugs as known to the art, such as sulfonylureas, acetohexamide, chlorpropamide, glipizide and glyburide, which produce insulin in the body. The term "glucose" includes pharmaceutically acceptable substitutes such as glucose polymers. The term "potassium" includes pharmaceutically acceptable salts of potassium. The term "thyroid" includes thyroid hormones including $T_3$ and $T_4$ and pharmaceutically acceptable combinations thereof.

Pathological conditions which may be treated by the compounds described herein include cancer, immunodeficiency syndromes, cancer chemotherapy drug resistance, and effects of immunodeficiencies such as symptoms of leprosy, tuberculosis, malaria, the concomitants of AIDS such as Kaposi's sarcoma, bronchial infections, and the like. As exemplified herein, the treatment of this invention resulted in significant prolongation of life beyond predicted life expectancies in canine subjects. An increase in unstimulated lymphocyte S-phase population of greater than five percent was seen, as was an increase of proliferative responsiveness of peripheral lymphocytes to poke weed mitogen of 266 percent. One subject with oral melanoma was completely cured, and substantial tumor reduction was seen in other subjects.

Potassium is the principal intracellular cation of most body tissues. It participates in a number of essential physiological processes including the maintenance of intracellular tonicity, transmission of nerve impulses, the contraction of cardiac, skeletal, and smooth muscle, cell proliferation, and the maintenance of normal renal function. The therapeutic procedure described involves repletion of intracellular potassium.

The immunosuppression produced by the collaboration of various growth factors and endocrine hormones can be reversed by artificially altering the hormonal mix to mimic that induced when the body is dealing with an infection. This hormonal therapy is aimed at forcing potassium into inactivated immune cells. Potassium enables the cells to engage in enzymatic reactions necessary to proliferation and activation. Glucose is also administered to Provide immune cells with the energy needed to pump out excess sodium and replace it with potassium.

The preferred immunoenhancement therapy of this invention calls for administration of insulin and preferably also thyroid hormone, and the infusion of glucose and potassium. A cholinergic agent such as pilocarpine is also preferably administered to stimulate potassium uptake by the cells and immune cell activation and proliferation. Bicarbonate can be used if necessary or desired to further aid in driving potassium into the cells.

Insulin causes cells to take up glucose and drives potassium into the cells. Thyroid and cholinergic agents add to this effect. Thyroid hormone stimulates ATPase and also facilitates exchange of extracellular potassium and intracellular sodium. Bicarbonate, aldosterone and desoxycorticosterone have the same effect on potassium and may be used if the patient fails to retain the infused potassium at desired levels.

This invention also provides pharmaceutical compositions comprising mixtures of glucose, potassium and insulin for intravenous infusion. The mixture may be supplied in powder form for rehydration, or in hydrated form. These compositions can be supplemented with additional insulin and thyroid. Cholinergic agents are preferably taken separately. Insulin and the cholinergic agent may be administered subcutaneously. Thyroid and the cholinergic agent may be taken in oral form.

This invention further provides pharmaceutical kits providing insulin, glucose and potassium and optionally thyroid, cholinergic agents, and bicarbonate in suitable dosages for self-administration to effectuate the therapeutic regime of this invention.

Methods and compositions for the topical application of the biotherapy of this invention are also provided.

Increasing intracellular potassium results in enhancement of the immune system, specifically by increasing proliferation of lymphocytes. It is also useful for stimulation of cancer cell apoptosis. Further, it is useful in resensitizing tumor cells which have become drug-resistant. The method is useful in vivo to provide increased numbers of lymphocytes for dealing with disease conditions such as tumors and foreign microorganisms and for increasing the challenged lymphocyte population prior to adoptive immunotherapy. The bioactive agents described herein may also be used in a culture medium for culturing cells in vitro for adoptive immunotherapy.

DETAILED DESCRIPTION OF THE PREFERRED EMBODIMENTS

A method is provided for enhancing or potentiating immune response in a mammal comprising increasing the intracellular potassium content of lymphocytes, preferably lymphocytes previously selected by antigen. This is accomplished in a preferred embodiment by administering to said mammal effective amounts of pharmaceutically acceptable insulin hormone, and potassium and glucose, for a sufficient period of time to increase the intracellular potassium such that an immune response is potentiated. Thyroid and a cholinergic agent may also be administered.

Increased intracellular potassium content of lymphocytes can be measured directly by means known to the art such as tests using the indicator dye PBFI (catalog number p-1265) (benzofuran 150 phthalate from Molecular Probes, Inc.). (See Kasner, S. E. and Ganz, M. B. (1992), "Regulation of intracellular potassium in mesangeal cells: a fluorescence analysis using the dye, PBFI," Amer. J. Physiol. 3:462–467.) The increase preferably brings the intracellular potassium levels to the maximum the cells are capable of maintaining. In an immunosuppressed patient prior to administering the biotherapy of this invention, these levels will be significantly less than maximum.

Effective amounts of each substance generally will be within the recommended dosage amounts provided below; however, dosage amounts can be adjusted by means known to the art and in accordance with the teachings hereof to achieve the desired objectives.

To enhance immune response ("immunoenhancement"), as is well-known in the art, means to increase the organism's capacity to respond to foreign antigens, i.e., those cells primed to attack foreign antigens are increased in number, activity, and ability to detect and destroy the foreign antigens. Strength of immune response is measured by standard tests including: direct measurement of peripheral blood lymphocytes by means known to the art; natural killer cell cytotoxicity assays (see, e.g. Provinciali M. et al (1992), "Optimization of Cytotoxic Assay by Target Cell Retention of the Fluorescent Dye Carboxyfluorescein Diacetate (CFDA) and Comparison with Convention $^{51}$Cr Release Assay," J. Immunol. Meth. 155:19–24), cell proliferation assays (see, e.g. Vollenweider, I. and Groseurth, P. J. (1992), "Comparison of the Four DNA Staining Fluorescence Dyes for Measuring Cell Proliferation of Lymphokine-activated Killer (LAK) Cells," J. Immunol. Meth. 149:133–135), immunoassays of immune cells and subsets (see, e.g. Loeffler, D. A., et al (1992), "Analysis of Distribution of Tumor- and Preneoplasia-Infiltrating Lymphocytes Using Simultaneous Hoechst 33342 Labeling and Immunophenotyping," Cytom. 13:169–174; Rivoltini, L., et al (1992), "Phenotypic and Functional Analysis of Lymphocytes Infiltrating Paediatric Tumors, with a Characterization of the Tumour Phenotype," Can. Immunol. Immunother. 34:241–251); or skin tests for cell-mediated immunity (see, e.g., Chang, A. E. et al (1993), "Clinical Observations on Adoptive Immunotherapy With Vaccine-primed T-Lymphocytes Secondarily Sensitized to Tumor In-vitro T-cells," Cancer Res. 53:1043–1050. Any statistically significant increase in strength of immune response as measured by the foregoing tests is considered "enhanced immune response" "immunoenhancement" or "immunopotentiation," as used herein. Greater than five percent increase in T-cells in S-phase have been achieved by the methods of this invention.

Enhanced immune response is also indicated by physical manifestations such as fever and inflammation, as well as healing of systemic and local infections, and reduction of symptoms in disease, i.e. decrease in tumor size, alleviation of symptoms of leprosy, tuberculosis, malaria, naphthous ulcers, herpetic and papillomatous warts, gingivitis, artherosclerosis, the concomitants of AIDS such as Kaposi's sarcoma, bronchial infections, and the like. Such physical manifestations also define "enhanced immune response," "immunoenhancement" or "immunopotentiation" as used herein.

The term "mammal" as used herein includes humans as well as animals used as sources of food, and nonfood animals, including cattle, swine, goats, marsupials, wild ungulates, dogs, horses, cats, whales, dolphins, zoo animals and other mammals.

The mammal which is the subject or patient of treatment by the methods and compositions of this invention is preferably one whose immune system is sluggish, suppressed or depressed, such as a mammal suffering from tumor, leprosy, tuberculosis, or the like. Symptoms of immunosuppression or weak immune systems include nonhealing wounds, chronic infections, and disease conditions, as well as assay results showing low numbers of T-cells in S-phase, or low response to skin tests using recall antigens.

The substances to be administered to said mammal in the practice of this invention should be in pharmaceutically acceptable form. That is, appropriate purities, dosage forms, chemical salts or chemical analogs, should be used as known to the art. Administration may be by any convenient route, intravenous, intramuscular, intralesional, oral, rectal, vaginal, topical, etc., as is known to the art, to produce the desired blood levels of the substances being administered. Such pharmaceutically acceptable forms and modes of administration are well-known to the art. The dosage of each substance should be high enough to produce the effects described below for each substance, but not so high as to cause death or permanent impairment of the animal.

In most cases, the course of treatment will be several days to a week or ten days, repeated as necessary, and the patient's reactions should be monitored and the dosages adjusted as required. Where proliferation of lymphocytes is required, rather than simple activation of existing lymphocytes, treatment periods of up to about twenty-one days may be required.

Glucose serves as an energy source and as an aid in intracellular transport of potassium ions. Glucose is administered in a dosage high enough to maintain normal to high blood glucose levels, as set forth above, but not so high as to cause severe hyperglycemia or diabetic coma.

Glucose infusions can cause fluid or solute overload resulting in dilution of serum electrolytes, overhydration, congestive states, or pulmonary edema. It is essential that clinical evaluations and laboratory determinations be conducted to monitor fluid balance, electrolyte concentrations, and acid-base balance during intravenous administration. Hyperglycemia and glycosuria may be functions of rate of administration or metabolic insufficiency. To minimize these conditions, a slow infusion rate should be used and blood and urine glucose should be monitored. Careful administration should be used to prevent extravasation. If thrombosis occurs during infusion, input should be stopped and the catheter removed. The maximum rate at which dextrose can be infused without producing glycosuria is 0.5 gm/kg/hour. At 0.8 gm/kg/hour 95% of infused glucose is retained. Parenterally administered glucose undergoes oxidation to carbon dioxide and water and provides 3.4 cal/gm of d-glucose monohydrates. Pharmaceutically acceptable concentrations of glucose are known to the art. A 5% dextrose solution is isotonic. (Five percent (5%) dextrose is 50 gm/L, 170 cal/L, or 253 mOsm/L).

In the preferred embodiment of this invention, if renal, liver function and blood sugar levels are normal, treatment is started with 5% glucose (dextrose). Infusion rate is maintained at less than 100 mL/hour. Preferably, glucose is administered in an amount of between about 4 g and about 20 g per kilogram of body weight per day, and more preferably between about 12 g and about 16 g per kilogram of body weight per day.

Potassium is the principal intracellular cation. Hypokalemia can occur from increases in renal excretion, in losses through GI tract, and from inadequate intake. Ninety-eight percent of total body potassium stores are intracellular. Potassium depletion of 1 mEq/L serum is equivalent to 100–200 mEq of potassium from total body stores. Symptoms of hypokalemia are weakness, fatigue, polydypsia, premature atrial and ventricular contractions, and prolonged QT interval. Normally 80–90% of potassium intake is excreted in the urine with the remainder voided in the stools and to a small extent in perspiration. Potassium should never be administered undiluted nor in states of hyperkalemia.

Potassium is administered in the form of pharmaceutically acceptable salts, e.g. chloride or acetate, in a dosage high enough to achieve total body repletion (i.e., mild hyperkalemia), but not so high as to cause cardiac depression, arrhythmias or arrest, preferably in an amount of between about 100 mEq and about 500 mEq per 75 kilograms of body weight per day, more preferably in an amount of between about 200 mEq and about 400 mEq per 75 kilograms of body weight per day. Potassium is preferably administered in the form of a chloride salt. Intravenous administration is preferred since the optimal dosage of potassium requires about two liters of fluid administered over an eight hour period, and potassium levels are measured in the blood or urine. The usual additive dilution is 40 mEq/L of IV fluid with a maximum of 80 mEq/L. ECG and electrolytes should be monitored for individual dosages. If serum potassium is greater than 2.5 mEq/L, then the maximum infusion rate should be about 10 mEq/hr. The maximum concentration should be about 40 mEq/L, and the maximum dose during a 24-hour period should be about 200 mEq. If serum potassium is less than about 2 mEq/L, then the maximum infusion rate should be about 40 mEq/L; the maximum concentration should be about 80 mEq/L; and the maximum dose during a 24-hour period should be about 400 mEq.

In a preferred embodiment of this invention, 30 mEq/L of potassium chloride is infused at a rate of less than 100 mL/hour. Potassium and glucose levels are monitored every 30 minutes in order to regulate infusion rates initially, then are measured twice daily thereafter. Potassium and sodium and occasionally uric acid are measured in a 24-hour urine collection prior to and at least twice during therapy.

Insulin is the principal hormone required for proper glucose utilization. Any pharmaceutically acceptable form of insulin or insulin equivalent as discussed above may be used. Regular insulin is preferred for rapid onset of action and short duration. In hyperkalemia it is known that mixtures of insulin and glucose (1 unit of insulin per 3 grams of dextrose) produce a shift of potassium ions into cells from the extracellular space and lower serum potassium levels. Insulin is administered in a dosage high enough to maintain blood premeal and bedtime glucose levels at about 80–140 mg/dL in the presence of added glucose as described above, but not so high as to cause hypoglycemic reaction or irreversible insulin shock, preferably in a subcutaneous amount of between about 0.05 U and about 2.4 U regular insulin per kilogram of body weight per day, more preferably in an amount of between about 0.25 U and about 1.5 U per kilogram of body weight per day. Insulin is preferably administered in the form of regular insulin with rapid (½-1 hour) onset, and is preferably monitored in the blood in terms of blood glucose levels. In a preferred embodiment hereof, administration of insulin is begun approximately 30 minutes after infusion of potassium, and glucose is started as described above, at a dosage of 0.5 U/kg/hour or 50 mL/hour (10 U per 1 L of solution).

Thyroid is administered in a dosage high enough to elevate $T_4$ levels to mild hyperthyroidism, e.g. 15 $\mu$g/dL (200 nmol/L), but not so high as to cause a hypermetabolic state, i.e. toxicity, preferably in an amount of between about 0.3 $\mu$g and about 4 $\mu$g per kilogram of body weight per day, more preferably in an amount of between about 1 $\mu$g and about 3 $\mu$g per kilogram of body weight per day. The usual maintenance dose of oral thyroid ($T_4$) is less than 0.2 mg/day. Parenteral doses are one-half of oral doses. Synthetic thyroid derivatives include levothyroxine ($T_4$), liothyronine ($T_3$), and four to one mixtures of $T_4$ and $T_3$ called liotrix (Thyrolar, trademark of Rorer-Rhone Poulenc Pharmaceuticals, Fort Washington, Pa.). The exact mechanism of action of thyroid hormones is not well understood, however, it is believed that most effects are exerted through control of DNA transcription and protein synthesis.

Potassium intracellular uptake is increased through thyroid hormone induction with new biosynthesis of $Na^+/K^+$ ATPase. The principal physiological effect of thyroid hormone is to increase the metabolic rate of body tissues with increases in oxygen consumption, respiratory rate, body temperature, cardiac output, heart rate, blood volume, rate of fat, protein, and carbohydrate metabolism, enzyme activity, and growth and activity. Thyroid hormones are also concerned with tissue differentiation and proliferation. Thyroid hormones are known to increase basal metabolic rate. The effect develops slowly but is prolonged. The onset begins within 48 hours and reaches a maximum in 8-10 days.

Thyroid is preferably administered in the form of levothyroxin ($T_4$) as an oral tablet or injection, and is measured in the blood in terms of $T_3$ and $T_4$ levels. Data suggests $T_4$ is the hormone of choice; $T_3$ has a more rapid onset of action but can produce thyrotoxic levels prior to $T_4$ intoxication. For rapid onset of action $T_3$ (liothryonine, available for example as Cytomel, Trademark of Smith, Kline & French Laboratories, Philadelphia, Pa.) or preparations of mixtures of $T_4$ and $T_3$ (available as Thyrolar, trademark of Rorer-Rhone Poulenc Pharmaceuticals, Fort Washington, Pa.) should be used. $T_3$ and $T_4$ are available, e.g., for reconstitution in sterile solution. $T_4$ is available, e.g., as Synthroid, Trademark of Boots-Flint, Inc., Lincolnshire, Ill.

Because thyroid takes up to 48 hours or more to exhibit an effect on the body, pretreatment with thyroid is recommended at least 48 hours in advance of the initiation of the treatment. The preferred method is to start thyroid hormone with liothyronine (Cytomel) 48 hours prior to infusions of potassium, insulin and glucose as discussed below. Thereafter liotrix 0.5 grain, equivalent to 25 $\mu$g $T_4$ and 6.25 $\mu$g $T_3$ per day should be given orally.

Contraindications for thyroid treatment include the following. Long-term $T_4$ usage has been associated with decreased bone density. Symptoms of toxicity include: cardiac—palpitations, tachycardia, angina pectoris, cardiac arrest; CNS—tremors, headache, nervousness, insomnia; GI—diarrhea and vomiting. Chronic excessive dosage may produce congestive heart failure (CHF) and angina pectoris.

Potassium transport mechanisms in lymphocytes are regulated by humoral and osmotic stimuli. The maintenance of high intracellular potassium levels is essential for optimum cell function for many types of cells including immune lymphocytes. In addition to glucose, insulin and thyroid hormone, membrane depolarization and electrochemical control via cholinergic receptors have been found to contribute to achieving intracellular potassium homeostasis. Pilocarpine is a well tolerated short acting (onset 15-30 minutes; duration 4-8 hours) parasympathomimetic agent. Higher concentrations have longer duration of action., In a preferred embodiment of this invention, a cholinergic agent, preferably pilocarpine, is administered to further stimulate potassium uptake by the cells and to stimulate proliferation of immune cells. Carbachol may be substituted for slightly longer action or if tolerance to pilocarpine develops (months to years). More potent and longer acting cholinergics include the acetylcholinesterase inhibitors. Another alternative is succinylcholine, a membrane depolarizing cholinergic. Pilocarpine is the cholinergic agent of choice since it will survive longer in the circulation, its effect is more sustained and it has a slightly greater impact on immune cells.

The cholinergic agent is administered preferably subcutaneously or intralesionally in a dosage high enough to stimulate potassium pumping but not so high as to induce undesirable side effects such as abdominal cramps, muscle weakness, urinary incontinence, bradycardia, diarrhea or bronco spasm. The cholinergic agent is administered in an amount between about 30 $\mu$g and 450 $\mu$g per day (based on a 70 kg patient). Preferably pilocarpine is administered in an amount of between about 35 and about 120 $\mu$g three times daily (about 1.5 $\mu$g/kg to about 5.1 $\mu$g/kg per day). Preferably the dosage is gradually increased to the maximum dosage over about a five-day period, with reduction if symptoms of toxicity occur. In case of acute toxicity atropine may be administered subcutaneously.

So long as blood potassium levels are maintained in the normal range and the body's capacity to handle the excess potassium is not exceeded, the thyroid and insulin will act to force potassium ions into the lymphocytes, and any excess potassium will be excreted. Continuous monitoring via ECG coupled with continuous potassium infusion can allow maximum dosages of potassium to be administered, with administration being halted or antidotes administered if adverse effects on the heart are observed. Antidotes for hyperkalemia include insulin and glucose, thyroid and bicarbonate as well as aldosterone and desoxycorticosterone, all of which act by pushing potassium into the cells, and out of the bloodstream. So long as the cells have not reached their capacity for uptake of potassium, these antidotes will be effective and can be administered until no further effect in lowering blood potassium levels is observed. Aldosterone and desoxycorticosterone also stimulate potassium excretion and may be used for this purpose.

The treatment with thyroid, insulin, glucose and potassium is preferably continued with dosages on a daily or several-times-daily basis as is convenient, until the desired level of immunopotentiation or immunoenhancement is reached as measured by any of the above tests. Preferably, the treatment is continued until physical manifestations of disease have been substantially alleviated or have disappeared. In one embodiment of this invention for treatment of tumors, the treatment is administered for five days and repeated at intervals of one to ten days until significant regression in the tumor has occurred. "Significant regression" means about fifty percent reduction in tumor mass.

Preferably the patient's blood levels of thyroid, insulin, glucose, and potassium are monitored at least daily during the course of treatment, and the dosages of each substance adjusted accordingly.

Thyroid ($T_4$) blood levels (measured by radioimmunoassay) are preferably maintained at serum levels of at least about 10 µg free/dL to about 18 µg free/dL serum, and preferably at least about 12 µg free/dL to about 15 µg free/dL. It is preferred that blood levels be those of mild hyperthyroidism, i.e., about 11 µg free/dL to about 14 µg free/dL. Serum $T_4$ levels can be used to test the effectiveness of all thyroid medications except $T_3$. The thyroid hormone suppression (THS) suppression test also can be used, as is known to the art to measure $T_3$ and $T_4$. If thyroid levels drop below this figure, dosage levels are increased as is known in the art until desired levels are reached. If thyroid levels rise above the optimal level, dosage is decreased. Physical reactions are also monitored and if headache, irritation, nervousness, sweating, tachycardia or other symptoms of toxicity as previously described happen as a reaction to the thyroid levels, management of overdosage is done as is known to the art, e.g., administration of thyroid is stopped and.

Insulin blood levels are preferably maintained at levels above normal, e.g. at least about 20 mIU/L. If insulin levels drop below this figure, dosage levels are increased as is known in the art until desired levels are reached. Glucose rather than insulin may be monitored in the blood. Preferably blood glucose levels are maintained at a level at least about 575 mg/L and preferably at least about 950 mg/L. If insulin levels rise above the optimal level, or glucose levels drop below the optimal level, glucose is administered until desired levels are reached. Physical reactions are also monitored and if hypoglycemia happens as a reaction to the insulin levels, it is preferred that, rather than reducing insulin dosage, glucose be administered, e.g., 50% or higher concentration solutions of glucose orally or sublingually. Commercial glucose solutions, glucagon and IV dextrose are useful antidotes to insulin. For insulin induced hypoglycemia, glucose may be administered according to the following: 10–25 gm glucose and repeated as necessary (adult); 250–500 mg/kg/dose (child); 5–10 mL of 25% dextrose solution for 5 kg infant.

Reduction in insulin causes potassium excretion into the urine, an indicator that potassium is not being distributed into the cells. Glucose in addition to the minimum required to maintain normal or high normal blood glucose levels may be administered to further facilitate potassium uptake and provide adequate intracellular energy for pumping. Inadvertent overdosage of insulin may lead to irreversible insulin shock. Allergic reactions to insulin are rare and may include erythema, swelling or pruritus. Such reactions usually resolve within a few days or weeks. In acute hypoglycemia, excision of the insulin injection site has been used to reverse worsening conditions.

Potassium blood levels are preferably maintained at least about 5.0 mEq/L. If potassium levels drop below this figure, dosage levels are increased as is known in the art until desired levels are reached. It is preferred that potassium be administered until the level of potassium excretion constant, and until blood potassium levels are no longer increasing. This typically occurs within about three to five days. If potassium levels rise above the optimal level, administration is stopped. Mild hyperkalemia (6.5 mEq/L serum) to moderate hyperkalemia (8 mEq/L serum) may be asymptomatic and manifested by increased serum potassium concentration and characteristic ECG changes. Muscular weakness and flaccid quadriplegia and respiratory paralysis occurs at serum concentrations greater than 8 mEq/L. Potassium intoxication includes the following signs and symptoms: flaccid paralysis; muscle or respiratory paralysis; weakness with mental confusion; mental confusion; hyponatremia; cardia arrhythmias; heart block and ECG abnormalities such as disappearance of P-waves; spreading and slowing of QRS complex with development of a biphasic curve and cardiac arrest, nausea and vomiting, abdominal pain, diarrhea. High plasma concentrations of potassium may cause death through cardiac depression, arrhythmias or arrest. Potassium must be monitored in plasma and urine, and by continuous or intermittent ECG. Potassium should not be used with any renal impairment or adrenal insufficiency. Potentially fatal hyperkalemia may be asymptomatic and may mimic hypokalemia. IV administration can cause fluid or solute overload resulting in dilution of serum electrolyte concentration and may overhydrate congested states or pulmonary edema. ECG changes accompanying potassium toxicity include: progressive increase in height and peaking of T-waves; lowering of R-waves; decrease in amplitude and ultimate disappearance of P-wave; prolongation of PR interval and QRS complex; shortening of QRS interval and ventricular fibrillation with death.

If hyperkalemia and ECG changes occur as a reaction to overdose of potassium, glucose and insulin are administered. Bicarbonate and calcium gluconate or chloride may also be administered. A recommended potassium overdose treatment is as follows. Terminate potassium input and begin infusion of 3 gm of dextrose per unit of regular insulin, (300–500 mL/hr 10% dextrose with 10–20 units of insulin/L); administer sodium bicarbonate, 50–100 mEq IV (further shifts potassium to intracellular stores), and administer calcium gluconate or chloride (10%), 10–100 mL, to reverse ECG changes.

Bicarbonate in pharmaceutically acceptable form may also be administered to enhance intracellular uptake of potassium. Preferably, bicarbonate is administered in the form of pharmaceutically acceptable salts, by intravenous infusion, or injection, orally or by other means known to the art. Bicarbonate is administered in a dosage high enough to push potassium into the cells, but not so high as to cause toxicity, preferably in an amount of between about 1.0 mEq and about 6.0 mEq per kilogram of body weight per day, more preferably in an amount of between about 2.0 mEq and about 5.0 mEq per kilogram of body weight per day. Blood gases should be monitored and treatment discontinued if indicated.

Aldosterone and/or its analog, desoxycorticosterone, in pharmaceutically acceptable form may also be administered. Aldosterone functions to further enhance potassium uptake. These substances force potassium into the cells and also stimulate its excretion. Aldosterone is normally produced in the body in response to elevated levels of potassium. Dosages are administered that are high enough to lower potassium serum levels, but not so high as to cause hypokalemia, preferably in an amount of between about 0.6 μg and about 20 μg per kilogram of body weight, more preferably in an amount of between about 2 μg and about 3 μg per kilogram of body weight per day. Desoxycorticosterone is preferably administered in the form of desoxycorticosterone acetate.

Pharmaceutical compositions comprising mixtures of insulin, potassium and glucose, and in the preferred embodiment, thyroid, and/or cholinergic agent, as disclosed above, in suitable form for IV, oral administration, injection or administration by other forms known to the art, are also provided by this invention.

In one embodiment of this invention, a mixture of insulin, potassium, and glucose is provided suitable for intravenous infusion. This mixture comprises between about 3.5 U and about 168 U insulin at standard pharmaceutically acceptable dosage concentrations, between about 98 mEq and about 490 mEq potassium, and between about 280 g and about 1400 g glucose (when thyroid is present it comprises between about 70 g and about 420 g and when pilocarpine or other cholinergic agent is present it comprises between about 105 μg and about 360 μg, all in a pharmaceutically-acceptable carrier as known to the art. The foregoing amounts are suitable for a 70 kg patient and may be adjusted, as is known in the art, in accordance with the patient's weight. The mixture is infused at a rate of between about 200 mL and about 800 mL/hour, for a period of about six to about twenty-four hours. Infusion is repeated daily, preferably for 3-10 days, then stopped for a period of about 7-10 days and repeated as required until potassium repletion is complete and immunoenhancement occurs. The relative amounts of each component in the mixture can be adjusted during treatment in accordance with measurements of blood concentrations of various components and occurrence of physical symptoms as described above.

The intravenous compositions may also be provided in dry powder form for daily reconstitution and preferably comprise between about 14 and about 28 g glucose, between about 98 and about 500 mEq potassium, between about 3 and about 170 U insulin, between about 80 and about 240 μg thyroid (liotrix), and between about 50 and about 80 mEq bicarbonate. The compositions are administered after adjusting dosages based on body weight and suitable dosages in accordance with the teachings herein.

In a further embodiment of this invention, a pharmaceutical kit is provided comprising multiple dosages of insulin, glucose and potassium suitable for self-administration at daily intervals by a patient of 70 kg in amounts providing maximum five-day dosages of between about 17.5 U and about 840 U for insulin; between about 1400 g and about 5600 g for glucose; and between about 490 mEq and about 2520 mEq for potassium. As will be appreciated by those skilled in the art, dosages may be adjusted based on the patient's weight.

Thyroid suitable for self-administration is optionally provided in such kit in amounts providing a maximum five-day dose of between about 350 μg and about 1.05 mg. Pilocarpine or other cholinergic agent may also be provided in amounts providing a maximum dose between about 10 μg three times per day and about 40 μg three times per day. Bicarbonate suitable for self-administration may also be provided in amounts providing a maximum five-day dose between about 70 g and about 140 g. As stated above, dosage amounts are given for a 70 kg patient and may be adjusted as appropriate.

The foregoing components of said pharmaceutical kit may be in any form suitable for self-administration by patients untrained in medicine, such as oral tablet or liquid form, or injectable form. Preferably all components available in oral form are provided in that form. In a preferred embodiment all the components are provided in oral form except for insulin which is readily available in self-injectable form.

The kit optionally contains a blood glucose monitor and additional glucose for use in correcting insulin-induced hypoglycemia. The kit may also include atropine in dosages suitable for correcting pilocarpine toxicity.

The biotherapy of this invention may be used prior to removal of lymphocytes for culturing for adoptive immunotherapy to increase the initial number of selected lymphocytes.

The method may also be adapted to produce a culture medium for culturing selected lymphocytes in vitro for adoptive immunotherapy. In vitro culture media for expansion of cells from vaccine-primed lymph nodes are supplemented with glucose, potassium, insulin, bicarbonate, and optionally pilocarpine, in order to increase the efficiency and immunological responsiveness of infused cells. In one embodiment of this invention about 50 mg/mL glucose, about 0.08 mEq/ml potassium, about 0.02 mEq/mL bicarbonate, about 10-100 U/mL insulin, about 1 μg/mL liothyronine, and about 10 mg/mL pilocarpine are added to the lymphocyte culture medium.

The biotherapy of this invention may also be applied topically in a skin cream or formulation comprising the above-described components. The topical formula is useful for treatment of superficial diseases and disorders arising from the integument. A formulation for such purpose may be an ointment, cream, gel, lotion or suppository, and may be compounded in a form suitable for spreading on the skin or applying to mucous membranes including nasal passages. A typical formulation of an oil-in-water cream for topical application to the skin comprises: Water phase: potassium chloride about 10-20 mEq; glucose about 5-10 g; liothyronine, about 50-100 μg; regular insulin, about 200-500 U; sodium bicarbonate about 1-2 g; pilocarpine about 1.5-5 mg; cross-linked acrylic acid copolymer (Carpobol 940 trademark of B. F. Goodrich, Inc., Cleveland, Ohio), about 100-250 mg; sodium hydroxymethylglycinate (Suttocide A trademark of GAF Chemicals Corp., Chatham, N.J.) about 300-500 mg; deionized water q.s. Oil phase: stearic acid about 2-4 g; glyceryl monostearate about 1-3 g; myristyl propionate about 1-5 mL; propylene glycol, about 3-7 mL; laureth-4 about 0.5-4 mL; mineral oil about 0.5-7 mL. Carpobol 940 is dissolved in the water phase to make a viscous solution to which water soluble ingredients are added. Then each phase is heated to 65°-70° C. and the oil phase is added slowly with stirring to the water phase. The mixture is mixed well and allowed to cool. Excess organic base, i.e., triethanolamine is added to complete gelation. Such topical preparation is then applied over and around the lesion as instructed by the physician and repeated daily for three weeks.

This invention lies in the methods and compositions disclosed herein, but without limitation to any theory, the following theoretical considerations are presented which will be of assistance in adjusting dosages and modifying the compositions and methods to produce clinically equivalent immunoenhancing or immunopotentiating therapies.

There are five interrelated factors affecting immunity:

1) Clonal selection for activation and proliferation of lymphocytes whose receptors match the antigenic challenge.

2) Immunomodulatory cytokines and lymphokines are released by damaged cells and by immune and inflammatory cells during an antigenic challenge. These growth factors are grouped together in the model provided herein as Aggressive Factors (AFs). They contribute in one way or another to an inflammatory or immune response. Some factors are chemotactic to macrophages and polymorphonuclear leukocytes. Others induce receptors on endothelial cells enabling circulating leukocytes to adhere to them; or they cause endothelial cells to part, allowing the leukocytes to leave the vascular compartment and enter the lesion. Still others enhance immunity by altering the behavior of macrophages. Many cytokines and lymphokines act as autocrines or paracrines, stimulating selected lymphocytes to take up nutrients and activate. Other factors induce angiogenesis or the laying down of a fibrin barricade. Other factors such as interferons and interleukins enhance major histocompatibility complex (MHC) expression.

Some AFs act as genuine hormones and affect distant tissues. Colony Stimulating Factors stimulate the bone marrow to produce more leukocytes. Interleukin-1 causes elevation of acute phase proteins, changes in circulating levels of plasma metals, bone and cartilage resorption, muscle proteolysis and production of collagen. In addition, the protein is carried to the hypothalamus where it bonds to receptors. The result is an elevated body temperature and an enhanced secretion of ACTH. The AFs serve as messenger molecules which inform the hypothalamus of an injury or antigenic challenge.

In summary, Aggressive Factors:
(a) Locally:
  i) Attract and stimulate leukocytes to activate and proliferate.
  ii) Stimulate production of a fibrin barricade.
  iii) Enhance immunogenicity of local cells.
(b) Distantly:
  i) Mobilize resources for leukocytes by stimulating proteolysis and lipolysis in peripheral tissues.
  ii) Stimulate the hypothalamus to produce an elevated body temperature and endocrine mix that favors immunity.

3) A set of proteins grouped together in the model presented herein as Regenerative Factors (RFs) is the third regulatory factor. These are secreted by various cells responsible for the restructuring of damaged tissue. RFs promote healing by stimulating cells such as fibroblasts and epidermal cells to take up amino acids, glucose, and fatty acids. Included in this group are Epidermal Growth Factor, Fibroblast Growth Factor, Transforming Growth Factors, -alpha and -beta, the somatomedins, and others. In one important sense, RFs have an opposite effect from that of AFs since they suppress inflammatory and immune reactions. TGF-beta is 1,000 times more powerful an immunosuppressant than cyclosporine. It is proposed in this model that these growth factors also reduce immunogenicity of local tissues by inhibiting the expression of MHC.

As with AFs, RFs are genuine hormones, affecting distant tissues such as adipocytes and myoblasts and producing a catabolic effect on peripheral tissues. It is proposed here that RFs also travel to the hypothalamus as a message to inform it that the body is dealing with a healing wound.

In summary, Regenerative Factors:
(a) Locally:
  (i) Stimulate cells involved in tissue restructuring to activate and proliferate.
  (ii) Inactivate leukocytes.
  (iii) Reduce immunogenicity by inhibiting expression of MHC.
(b) Distantly:
  (i) Mobilize resources for the healing wound by stimulating proteolysis and lipolysis in peripheral tissues.
  (ii) Stimulate the hypothalamus to induce an endocrine mix that favors healing.

4) The hypothalamus-pituitary-endocrine system is the fourth factor. Although it has been known for some time that certain hormones powerfully affect immunity, this has not been integrated into a comprehensive model of immunoregulation. Endocrine hormones are clearly part of an overall regulatory system. In fact, the neuroendocrine system constitutes an entirely different dimension of immunoregulation.

5) The central nervous system is the fifth factor. Not only does the hypothalamus largely control the endocrine system, but the CNS enters actively into an immune reaction. For example, during a systemic infection, the CNS causes the release of norepinephrine from nerve endings in peripheral tissues. That prevents muscle and fat cells from competing with immune cells for serum glucose and electrolytes. The central nervous system also causes release of cholinergic and adrenergic agents into an inflammatory lesion or healing wound. Lymph organs are also innervated and are thus subject to regulation by these neurohormones.

Curiously, in an inflammation, infection or healing wound, the endocrine mix is always catabolic and immunosuppressive. That is important because in each of those situations nutrients must be robbed from peripheral tissues and provided to the rapidly dividing cells involved either in the immune reaction or in healing. Also, nutrients must not be diverted to immune cells other than those specifically involved in the major challenge.

The endocrine mix induced by the hypothalamus acts synergistically with the RFs and AFs increasing the effects of those factors. Thus, neither the levels of endocrine hormones nor the levels of RFs or AFs need be so high as to damage the organism. The cells actually involved in healing, inflammation or immunity are able to overcome the catabolic and immunosuppressive effect of the hormonal environment because they are receiving direct stimulation by AFs or RFs. In the case of an immune response, the lymphocyte clones selected by the antigens are past the point in their cycles where any but the highest levels of endocrine hormones (such as cortisol) can affect them, but other cells, selected by antigen after this immunosuppressive endocrine environment is in effect, are unable to activate. This produces the phenomenon of antigenic competition in which an existing infection will cause the body to mount an inadequate response to a second antigenic challenge.

The body regulates the activation of immune and inflammatory cells by denying or providing essential materials: amino acids, fatty acids, glucose and electrolytes. It does that by controlling ionic fluxes. When a lymphocyte is selected by antigen, the first detectable effect is an efflux of potassium and a compensating influx of sodium, down the electrochemical gradient. This influx of sodium brings in fatty and amino acids and glucose. Before the lymphocyte can then respond to stimulation by cytokines, it must restore intracellular levels of potassium to normal with the sodium/potassium pump ($Na^+K^+$ ATPase), an energy-dependent action. A number of investigators have shown that blockage of the $Na^+K^+$ ATPase will prevent the cell from activating or proliferating. (See, e.g. Harold, F. M. (1986), The Vital Force, A Study of Bioenergetics, W. H. Freeman and Co., New York, p. 332; Handwerger, B. S. and Douglas, S. D. (1980), "Cell Biology of Blastogenesis," in The Cell Biology of Inflammation, (G. Weissmann, ed.), Elsevier, New York/North-Holland Biomedical Press, Amsterdam, p. 654; Segel, G. B. and Lichtman, M. A. (1976), "Potassium Transport in Human Blood Lymphocytes Treated with Phytohemagglutinin," J. Clin. Investigation 58:1358–1369; Quastel, M. R. and Kaplan, J. G. (1970) "Early Stimulation of Potassium Uptake in Lymphocytes Treated with PHA," Expl. Cell. Res. 63:230–233.)

Therefore, in addition to the regulation already imposed by antigenic selection and stimulation or inhibition by modulatory cytokines, the body is able to further regulate immunity through glucoregulatory hormones. By denying a leukocyte glucose, the body denies the cell the energy it needs to restore intracellular potassium levels. Glucoregulatory hormones include cortisol, insulin, glucagon, growth hormone and thyroid in different combinations. The hormonal profile produced during an infection differs from that produced during the healing of a wound. During an infection, the body causes an increased secretion of growth hormone, cortisol, thyroxine, aldosterone, insulin and glucagon. When a wound is healing, the liver produces high levels of somatomedins which are believed to compete with insulin for receptor sites. Insulin drops to normal or below, thus depriving lymphocytes of the stimulation they need if challenged by antigen. Levels of glucagon drop, and thyroxine and aldosterone decline slowly.

It has not been previously known why malignant cells generally are not significantly antigenic to elicit an effective immune response in humans. It is known that immune and inflammatory cells do invade tumors and do release modulating cytokines. However, invading leukocytes not only fail to damage the tissue but even, on occasion, seem to contribute to tumor growth. Attempts to stimulate the immune system to attack malignant cells have largely failed or produced unacceptable toxicity.

In this model, as applied to tumors, the body restrains the immune reaction to a tumor because the RFs that are reaching the hypothalamus signal a healing wound. Tumor cells release growth factors in the same way as dividing cells of a healing wound. These growth factors give autocrine and paracrine stimulation to tumor cells to take up amino acids, fatty acids, glucose and electrolytes. However, at the same time, these growth factors have a suppressive effect on immune cells, either directly or through reduction in tumor cell production of MHC. Furthermore, these same growth factors interact in the hypothalamus as if from a healing wound. This induces the hypothalamus to signal the elaboration of an endocrine mix that favors "healing," i.e., tumor growth and cachexia, thus further suppressing immunity and MHC expression.

The larger the tumor, the more growth factors it releases. The more RFs that reach the hypothalamus, the harder the body tries to support the "healing wound." The endocrine mix induced by the hypothalamus collaborates with the RFs being released by the tumor.

Together they produce:

1) loss of fat and protein from peripheral tissues, (i.e., cachexia).

2) Rapid growth of the tumor (wound).

3) Inactivation of those leukocytes reaching the tumor (by promoting cellular loss of potassium and replacement of sodium).

4) Reduction of immunogenicity in tumor tissues by suppression of MHC expression.

The treatment system disclosed herein is designed to provide the body with the hormonal mix which occurs during infection rather than one which occurs during wound healing. The biotherapy of this invention is based on the idea that the body regulates immunity by controlling ionic fluxes. Through the neuroendocrine system, the brain down-regulates systemic immunity by causing the cells to fill with sodium, denying the cell the energy it needs to restore potassium levels to normal. Thus, lymphocytes and monocytes, which cannot pump sodium out and potassium in, cannot recover from either antigen or cytokine stimulation, since both cause efflux of potassium and influx of sodium. The cell cannot move on to full activation and proliferation. By forcing potassium into immune cells (with bicarbonate and insulin) and providing stimuli to the $Na^+K^+$ ATPase (with insulin, thyroid, cholinergic agents), and energy for pumping (glucose), immunosuppression is overcome. This leads to an effective attack on pathogens or tumor.

There is reason to believe that both phagocytes and lymphocytes come into contact with cholinergic agents in a wound or inflammatory lesion. (Ignarro, L. J. (1975), "Regulation of Lysosomal Enzyme Release by Prostaglandins, Autonomic Neurohormones and Cyclic Nucleotides," in Lysosomes in Biology and Pathology (Dingle, J. T. and Dean, R. T., eds.) at 517 ff.) Also, the thymus, spleen, lymph nodes and other peripheral lymphoid organs are known to be innervated by both cholinergic and adrenergic nerve fibers. Thus, the autonomic nervous system has contact with and presumably regulates the function of T-cells resident in lymphoid organs. (Hadden, J. W. (1987), "Neuroendocrine Modulation of the Thymus-Dependent Immune System," Annals of the N.Y. Acad of Sciences 496:39–48. It is also established that the molecular reaction of acetylcholine with its recognition sites causes a rapid increase in ion conductance in mammalian neuromuscular junctions. (Tiedt, T. N. et al., (1979) "Voltage- and Time-Dependent Actions of Piperocaine on the Ion Channel of the Acetylcholine Receptor," Molec. Pharmacology 16:909–921. It is disclosed herein that cholinergic agents participate in regulation of immunity, providing necessary stimuli and the same ionic fluxes caused by antigen selection, cytokine stimulation and insulin. Insulin, cholinergic agents and thyroid work synergistically to stimulate cells, restore ionic integrity and move immune and inflammatory cells forward in their cycles of activation and proliferation. Thus, administering cholinergic agents in concert with insulin, thyroid, glucose and potassium chloride (with bicarbonate to assist in moving the potassium into the cells) stimulates lymphocytes to attack and destroy the tumor.

Because thyroid acts slowly, the patient may be pretreated with thyroid two to three days in advance of the remainder of the treatment in order to allow time to achieve stabilized thyroid blood levels sufficient to stimulate the Na+K+ ATPase.

It is desirable prior to treatment to bring the patient up to normal in nutrition as lack of adequate nutrition can inhibit an immune response. Cancer patients are frequently cachexic, and thus the patient may be given nutritional supplements to bring about a more prompt response to the treatment of this invention.

EXAMPLES

Example 1. "Macho."

A six-year-old male Rottweiler dog was diagnosed with hemangiosarcoma from excisional biopsy by a qualified veterinary pathologist. The tumor measured 10 cm×12.5 cm. The animal had lost 17 pounds and was weak. Surgery plus chemotherapy was recommended. Usual life expectancy for this condition is six to twelve months, but due to the size of the tumor and the animal's overall condition, its life expectancy was only thirty to sixty days. The patient's owners agreed to the new treatment protocol for immunoenhancement as described in this application.

On the day before treatment was to begin, the dog received 0.4 mg of oral thyroid as levothyroxin. On treatment day (day 1) and for two more days, the dog received a) 2.8 L of potassium (30 mEq/L) or 0.25 mEq/kg/hr b) 0.9 mg of levothyroxin and c) 11.4 Units (or 0.11 mL) of regular insulin. The treatment took place over an eight-hour period each day.

On days 1 and 2 all vital signs were normal—body temperature, blood glucose, ECG, and respiration rate. After the first day the animal was sent home at night and returned to the clinic the next day for treatment and/or observation. Beginning on day 2, body temperature began to increase gradually from an average 101.2° F. to 104° F. beginning on day 4. Therapy was halted on day 4 and replaced with an infusion of 3 L of normal saline. Therapy was restarted on day 5 as body temperature began to subside.

The tumor began to swell and became tender and painful to touch on day 2. By day 4, the tumor had flattened. Aspiration biopsy on day 8 was negative for tumor cells on day 8, and the animal's health and well-being had greatly improved. The tumor was no longer painful to touch. The dog was continued on 0.4 mg. of thyroid 2× daily to correct a deficiency. An excisional biopsy on day 27 showed no evidence of tumor in any section consistent with infarcted necrotic hemangiosarcoma. Well-being of the animal had greatly improved. Approximately five months later the tumor recurred. Treatment was administered and the tumor regressed, the dog became frisky and experienced enhanced well-being. Approximately three months later the tumor again began to grow. The dog's owners declined further treatment and elected to euthanize their pet approximately three months later. The dog's survival time was eleven months.

Techniques of flow cytometric analysis of DNA content and distribution (Vollenweider, I. and Groseurth, P. J. (1992), "Comparison of the Four DNA Staining Fluorescence Dyes for Measuring Cell Proliferation of Lymphokine-activated Killer (LAK) Cells," J. Immunol. Meth. 149:133–135) and monoclonal antibodies to CD4 helper and CD8 suppressor immune cell lymphocytes (Loeffler, D. A., et al (1992), "Analysis of Distribution of Tumor- and Preneoplasia-Infiltrating Lymphocytes Using Simultaneous Hoechst 33342 Labeling and Immunophenotyping," Cytom. 13:169–174; Rivoltini, L., et al (1992), "Phenotypic and Functional Analysis of Lymphocytes Infiltrating Paediatric Tumors, with a Characterization of the Tumour Phenotype," Can. Immunol. Immunother. 34:241–251), indicated that after three courses of treatment, Macho had increased proliferative responsiveness of his peripheral lymphocytes to poke weed mitogen of 266% and a CD4 to CD8 ratio of 1.81.

Example 2. "Kody."

A 14-year old Sheltie dog (Table 1) was diagnosed with melanoma of the oral cavity and with no metastatic lesions to abdomen or chest. A standard blood chemistry profile indicated below normal number of lymphocytes and eosinophiles. The dog received medication according to protocol as per the regimen outlined in Table 2. The treatment was for five days. A second treatment of four days' duration was started eight weeks later. No drug-associated adverse effects were observed, i.e. ECG remained normal. No evidence of recurrence has been seen and lymph nodes remain normal as of this writing, eleven months post-treatment.

Example 3 Summary of Canine Tests.

Eight dogs from 4 to 14 years old with mixed tumor types as specified in Table 1 were entered into clinical investigation. All animals presented with advanced disease of moderate duration. Diagnosis was confirmed histologically and/or radiographically by a Board-certified veterinary pathologist. The study was conducted by professionally trained veterinarians in a private practice setting. The ability of the compositions of this invention to modify the clinical course of these tumors is verified by prolongation of life and disease-free intervals. The life expectancy was based on best clinical opinion at the time of initiation of the studies. Some subjects were prematurely euthanized by their owners. The life survival profile is shown in FIG. 1.

TABLE 1

| Patient (age, breed, sex) | Diagnosis (date) | Therapy (avg. days, courses and regimen**) | Actual Survival (days) | Expected Life Span (days) |
| --- | --- | --- | --- | --- |
| Macho (7, Rottweiler-male) | hemangio-sarcoma (6/19/92) | 3 for 9 courses regimen: A-E | 351* | 60 |
| Kody (14, Sheltie-n/male) | oral melanoma (9/12/92) | 4 for 2 courses regimen: A, F | (still alive) >321 days at this writing | 150 |
| Starr | hemangiosar | 6 for | 24* | 45 |

TABLE 1-continued

| Patient (age, breed, sex) | Diagnosis (date) | Therapy (avg. days, courses and regimen**) | Actual Survival (days) | Expected Life Span (days) |
|---|---|---|---|---|
| (10, Lab-male) | coma (10/16/92) | 1 course regimen: A | | |
| Cotton (10, Lab-male) | mast cell (10/21/92) | 5 for 1 course regimen: A | 65* | 60 |
| Bergen (6, Sheltie-male) | lymphosar-coma (10/23/92) | 8 for 2 courses regimen: A, G | 66* | 45 |
| Max (4, Schnauzer-male) | lymphosar-coma (10/23/92) | 5 for 2 courses regimen: B | 51* | 45 |
| Morgan (4, mixed-male) | lymphosar-coma (10/14/92) | 4 for 4 courses regimen: J, K | 90 | 45 |
| Diddle (4, mixed-s/female) | lymphosar-coma (12/1/92) | 3 for 5 courses regimen: A, E, H, I | 66* | 45 |

*Euthanized at owner's request.
See Table 2.

Each animal received a complete physical, hematological, electrocardial and radiological exam prior to acceptance into the study. After diagnosis and review of radiological and biopsy reports, the animals were scheduled for clinical investigation. Each owner of the animal signed an informed consent acknowledging the investigative nature of the clinical project.

At least one week prior to entering the clinical project the animals received a priming dose of thyroid hormone. On the morning of each treatment day the animals began their potassium and glucose infusions at the specified rate and amount as recorded in Table 2. The animals also received thyroid hormone and insulin. At midday and at end of each day, animals received their second and third doses of insulin; thyroid hormone was administered prior to going home or the dose was administered at home by owner. Occasionally, the dose of insulin at midday was withheld because of hypoglycemia. In other rare instances of hypoglycemia, the animals were administered glucose syrup.

All animals experienced improved vigor and alertness after receiving the regimen, appetite improved, and owners reported a better well-being for their animal. None of the dogs experienced any cardiopulmonary maladies during the course or after the clinical investigation. Three of eight dogs experienced diarrhea with blood usually after the first day of the clinical project.

Six of eight animals received multiple courses of the regimen as outlined in Table 2, the average being three such courses about three weeks apart. All but one animal has died, the second longest-lived survived nearly twelve months in the face of a usual life expectancy of only two to three months for its disease. The canine with melanoma of the oral cavity is still alive at eleven months. Six animals were euthanized by their owners before completing the investigation or before adequate follow-up could be made.

Immunotyping (Loeffler, D. A., et al (1992), "Analysis of Distribution of Tumor- and Preneoplasia-Infiltrating Lymphocytes Using Simultaneous Hoechst 33342 Labeling and Immunophenotyping," Cytom. 13:169–174; Rivoltini, L., et al (1992), "Phenotypic and Functional Analysis of Lymphocytes Infiltrating Paediatric Tumors, with a Characterization of the Tumour Phenotype," Can. Immunol. Immunother. 34:241–251) of lymphocytes from three dogs during the course of their treatment indicated an elevation in CD4/CD8 ratio (>3) with one dog showing possible evidence of in vivo immune priming; an increase in unstimulated lymphocyte S-phase population of >5%.

In conclusion, most animals presented with widespread disease with solid tumors of considerable size and life expectancies of less than sixty days. One-fourth of the treated animals experienced life expectancy greater than their clinical prognosis and most experienced an improvement in quality of life during the clinical project and afterwards. The absolute survival for most animals is unknown due to owners' election to euthanize their pets.

TABLE 2

| METHOD | INSULIN U/lb 3X | THYROID μg/10lb 2X | POTASSIUM mEq/L |
|---|---|---|---|
| A | 0.10 | Levothyroid (T$_4$) 100 μg | 30 (84 mEq/day) |
| B | 0.10 | Liothyroid (T$_3$) 25 μg | 50 (70 mEQ/day) |
| C | 0.18 | Liotrix; (T$_4$/T$_3$) 200 μg T$_4$/50 μg T$_3$ | 50 (70 mEq/day) |
| D | 0.10 | Liotrix; (T$_4$/T$_3$) 216 μg T$_4$/55 μg T$_3$ | 50 (70 mEq/day) |
| E | 0.10 | Levothyroid (T$_3$) 100 Liotrix (T$_4$/T$_3$) 216 μg T$_4$/55 μg T$_3$ | 50 (70 mEq/day) |
| F | 0.10 | T$_4$/T$_3$ 50 μg T$_4$/11 μg T$_3$ | 50 (35 mEq/day) |
| G | 0.14 | Liothyroid (T$_3$) 25 μg | 50 (70 mEq/day) |
| H | 0.20 | Liothyroid (T$_3$) 25 μg | 50 (70 mEqlday) |
| I | 0.10 | Liothyroid(pre)(T$_3$) 55 μg Liotrix(T$_4$/T$_3$) 210 μg T$_4$/58 μg T$_3$ | 50 (70 mEq/day) |
| J | 0.14 | Liotrix (T$_4$/T$_3$) 80 μg T$_4$/20 μg T$_3$ Liothyroid (T$_3$) 25 μg | 50 (70 mEq/day |
| K | 0.10 | Liothyroid(pre) (T$_3$) 50 μg (T$_4$/T$_3$) 200 μg T$_4$/50 μg T$_3$ | 50 (70 mEq/day) |

Example 4. Human Biotherapy Regimen.

Seven days prior to beginning biotherapy a complete hematology workup is obtained including tests of T$_3$ and T$_4$ fasting insulin and glucose levels. Thyroid administration (Liotrix, 22.5 mg per 10 lb. twice daily in a.m. and p.m.) is begun and adjusted daily according to schedule, Table 3.

Three days prior to beginning biotherapy, an insulin challenge test is conducted as is known to the art to determine the patient's ability to tolerate insulin.

The biotherapy is administered for five days as shown in Table 3. Administer water ad lib and food at midday and in evening.

TABLE 3

| AGENT | DAILY THERAPY | DIVIDED DOSE | FREQUENCY | ADJUSTMENTS |
|---|---|---|---|---|
| Liotrix* | 45 μg/10 lb/day | 23 μg/10 lb | AM and PM | Yes |
| Potassium** | 1.6 mEq/lb/day | 50 mEq/L | continuous | |
| 5% Dextrose | 30 mL/lb/day | | continuous | |
| Insulin*** | 0.6 U/lb/day | 0.2 U/lb | AM, Noon, PM | Yes |
| Pilocarpine**** | escalating | | three × daily | Yes |
| Bicarbonate# | 240 mg/lb/day | | continuous | |

*Start 1 week before treatment and continue during and after treatment according to instructions.
**In 5% dextrose and water (no saline).
***At end of day (EOD), administer 0.5 cc 50% dextrose before discharge.
****Use Isopto Carpine 10% (15 mL) sterile ophthalmic solution via subcutaneous injection in escalating scheme (see below), start on Day 2 of therapy.
Administer together with potassium infusion 1.5% Potassium Bicarbonate.
For each eight hour day, total potassium (K) is 70 mEq; Glucose is 70 gm; Bicarbonate is 21 gm. Infusion is 175 mL fluid/hr.

Adjustments:

Liotrix (Thyroid): Decrease or increase 1.5 μg/10 lbs for each 10 ng/dL of $T_3$ above or below 200 ng/dL, respectively.

Insulin: Decrease or increase 44 mU/kg for each 10 mg/dL of glucose below or above 50 mg/dL, respectively.

Pilocarpine: Pilocarpine is available as a sterile ophthalmic solution in many generic and brand names. It is recommended to start at 10% concentration, available in 15 mL size. Transient stinging and irritation may occur at injection site. For injection volumes in excess of 0.1 cc, use multiple injection sites.

Dosage of pilocarpine is individualized as shown by the escalation scheme shown in Table 4.

TABLE 4

| DAY | INJECTION VOLUME** | DAILY μG PILOCARPINE |
|---|---|---|
| 1 | 0 ML | 0 |
| 2 | 0.1 mL × TID | 30 |
| 3 | 2 sites × 0.1 mL × TID | 60 |
| 4 | 3 sites × 0.1 mL × TID | 90 |
| 5 | 4 sites × 0.1 mL × TID | 120 |

*If treatment extends beyond 5 days, HOLD at last dose
**If signs of systemic toxicity occur, DECREASE dose to PREVIOUS level and HOLD The patient is monitored as shown in Table 5.

TABLE 5

| TIME | MEASUREMENT |
|---|---|
| AM/PM | Body weight, temperature |
| AM/NOON/PM | Glucose, Respiration, Heart Rate |
| PM | Cardiogram, Blood, Urine, Insulin |

Modifications are made in the biotherapy as follows:

If hypoglycemia occurs, adjust next dose according to protocol (above) and if desired, administer 0.5 cc 50% glucose syrup. A tube of 50% glucose syrup may be provided for home use if necessary.

Diarrhea may occur during treatment and may be controlled by standard remedies. In case of severe diarrhea, the treatment should be discontinued. Excessive insulin may cause hypoglycemia which can be treated by glucose administration. Bicarbonate may cause tachycardia, and should be discontinued if life-threatening. If tachycardia persists, possibly due to potassium, discontinue biotherapy.

In case of toxicity, antidotes may be administered as shown in Table 6.

TABLE 6

| ITEM | RANGE | TOXICITY | ANTIDOTE* |
|---|---|---|---|
| GLUCOSE mg/dL | >120 | hyperglycemia | Carefully administer insulin |
| THYROID T4 μg/dL | >20 | chest pain, fast or irregular heart beat, shortness of breath | Withdraw |
| POTASSIUM mEq/L | >6 | numbness in extremities, confusion irregular heart beat, weakness | Administer dextrose 3 g per unit of insulin and bicarbonate |
| BICARBONATE mEq/L | >24 | tachycardia, alkylosis | Withdraw |
| INSULIN mU/dL | >70 | confusion, drowsiness, headache, nausea | 0.5 cc 50% glucose gel or syrup |
| PILOCARPINE μg/dL | >8 | increased sweating, muscle tremors, nausea, vomiting, watering of the mouth | atropine sc |

*Stop medications, monitor ECG

All references cited in the foregoing specification and examples are incorporated in their entirety by reference herein.

Those of ordinary skill in the art will appreciate that alternative techniques, procedures, methods and reagents other than those specifically described in the foregoing examples can be readily employed or substituted to achieve the objects of the present invention, i.e., compositions and treatment methods for immunoenhancement or immunopotentiation, and alleviations of physical symptoms, such as reduction in tumor size and alleviation of symptoms of leprosy, malaria, herpes, shingles, tuberculosis, naphthous ulcers, herpetic and papillomatous warts, AIDS, gingivitis, atherosclerosis, and the like. Alternative, but functionally equivalent, pharmaceutical compositions including hormones, vitamins and minerals, and methods will be readily apparent to those of ordinary skill in the art and can be applied to the present invention without expense of undue experimentation. All such alternatives, variations and equivalents are to be considered to be encompassed within the spirit and scope of the present invention.

I claim:

1. A method for increasing the intracellular potassium content of lymphocytes of a mammal comprising administering to said mammal glucose in the amount of about 4 g–20 g/kg/day, insulin in an amount effective to maintain blood pre-meal and bedtime glucose at about 80–140 mg/dL, potassium in an amount effective to maintain blood levels at least about 5.0 mEq/L, and thyroid in an amount effective to elevate $T_4$ levels to mild hyperthyroidism, whereby intracellular potassium content of lymphocytes is increased.

2. A method for increasing the intracellular potassium content of lymphocytes of a mammal comprising administering to said mammal glucose in the amount of about 4 g–20 g/kg/day, insulin in an amount effective to maintain blood pre-meal and bedtime glucose at about 80–140 mg/dL, potassium in an amount effective to maintain blood levels at least about 5.0 mEq/L, and bicarbonate in an amount of at least about 1.0 mEq/kg per day, whereby intracellular potassium content of lymphocytes is increased.

3. A method for increasing the intracellular potassium content of lymphocytes of a mammal comprising administering to said mammal glucose in the amount of about 4 g–20 g/kg/day, insulin in an amount effective to maintain blood pre-meal and bedtime glucose at about 80–140 mg/dL, potassium in an amount effective to maintain blood levels at least about 5.0 mEq/L, and a cholinergic agent in an amount of at least about 105 µg per day, whereby intracellular potassium content of lymphocytes is increased.

4. The method of claim 3 in which said cholinergic agent is pilocarpine.

5. The method of claim 1 wherein said insulin, glucose and potassium are administered for at least about five days.

6. A method for increasing the intracellular potassium content of lymphocytes of a mammal comprising administering to said mammal glucose in the amount of about 4 g–20 g/kg/day, insulin in an amount effective to maintain blood pre-meal and bedtime glucose at about 80–140 mg/dL, potassium in an amount effective to maintain blood levels at least about 5.0 mEq/L, wherein one unit of insulin per three grams of glucose is administered, whereby intracellular potassium content of lymphocytes is increased.

7. A method for increasing the intracellular potassium content of lymphocytes of a mammal comprising administering to said mammal glucose in the amount of about 4 g–20 g/kg/day, insulin in an amount effective to maintain blood pre-meal and bedtime glucose at about 80–140 mg/dL, and potassium chloride or potassium acetate in an amount effective to maintain blood levels at least about 5.0 mEq/L, whereby intracellular potassium content of lymphocytes is increased.

* * * * *